United States Patent [19]

Berg

[11] Patent Number: 5,360,520
[45] Date of Patent: Nov. 1, 1994

[54] SEPARATION OF 2-BUTANOL FROM T-AMYL ALCOHOL BY EXTRACTIVE DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 181,785

[22] Filed: Jan. 18, 1994

[51] Int. Cl.$^5$ .................... B01D 3/40; C07C 29/84
[52] U.S. Cl. .............................. 203/57; 203/58; 203/60; 203/62; 568/913; 568/918
[58] Field of Search ............... 203/57, 58, 60, 62; 568/913, 918

[56] References Cited

U.S. PATENT DOCUMENTS

| | | | |
|---|---|---|---|
| 2,551,584 | 5/1951 | Carlson et al. | 203/58 |
| 2,595,805 | 5/1952 | Morrell et al. | 203/84 |
| 4,693,787 | 9/1987 | Berg et al. | 203/57 |
| 4,693,788 | 9/1987 | Berg et al. | 203/57 |
| 4,756,803 | 7/1988 | Berg | 203/60 |
| 4,935,103 | 6/1990 | Berg et al. | 203/60 |

Primary Examiner—Wilbur Bascomb, Jr.

[57] ABSTRACT

2-Butanol is difficult to separate from t-amyl alcohol by conventional distillation or rectification because of the proximity of their boiling points. 2-Butanol can be readily separated from t-amyl alcohol by extractive distillation. Effective agents are methyl caproate, adiponitrile and cyclopentanone.

1 Claim, No Drawings

SEPARATION OF 2-BUTANOL FROM T-AMYL ALCOHOL BY EXTRACTIVE DISTILLATION

FIELD OF THE INVENTION

This invention relates to a method for separating 2-butanol from t-amyl alcohol using certain organic liquids as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the lowest boiling component.

At the bottom of a continuous column, the less volatile components of the close boiling mixtures and the extractive agent are continuously removed from the column. The usual methods of separation of these components are the use of another rectification column, cooling and phase separation, or solvent extraction.

There are a number of commercial processes which produce complex mixtures of oxygenated organic compounds, e.g. the Fischer-Tropsch process In this mixture, a series of homologous alcohols are often produced. Two of the commonest alcohols in this mixture are 2-butanol and t-amyl alcohol. 2-Butanol boils at 99.5° C. and t-amyl alcohol at 102.4° C. The relative volatility between these two is 1.13 which makes it very difficult to separate them by conventional rectification. Extractive distillation would be an attractive method of effecting the separation of 2-butanol from t-amyl alcohol if agents can be found that (1) will create a large apparent relative volatility between 2-butanol and t-amyl alcohol and (2) are easy to recover from 2-butanol Table 1 shows the relative volatility required to obtain 99% purity. With no agent, the relative volatility is 1.13 and 100 actual plates are required. With an agent giving a relative volatility of 1.3, only 47 plates are required.

OBJECTIVE OF THE INVENTION

The object of this invention is to provide a process or method of extractive distillation that will enhance the relative volatility of 2-butanol from t-amyl alcohol in their separation in a rectification column. It is a further object of this invention to identify organic compounds which in addition to the above constraints, are stable, can be separated from 2-butanol and recycled to the extractive column with little decomposition.

TABLE 1

Theoretical and Actual Plates Required vs. Relative Volatility for 2-Butanol - t-Amyl Alcohol Separation

| Relative Volatility | Theoretical Plates Required At Total Reflux, 99% Purity | Actual Plates Required 75% Efficiency |
|---|---|---|
| 1.13 | 75 | 100 |
| 1.2 | 51 | 68 |
| 1.25 | 41 | 55 |
| 1.3 | 35 | 47 |

SUMMARY OF THE INVENTION

The objects of this invention are to provide a process for separating 2-butanol from t-amyl alcohol which entails the use of certain organic compounds as the agent in extractive distillation.

DETAILED DESCRIPTION OF THE INVENTION

TABLE 2

Effective Extractive Distillation Agents For Separating 2-Butanol From t-Amyl Alcohol

| Compounds | Relative Volatility |
|---|---|
| None | 1.13 |
| Acetophenone | 1.2 |
| Adiponitrile | 1.3 |
| Methyl caproate | 1.25 |
| Ethyl caproate | 1.2 |
| Propyl caproate | 1.2 |
| Hexyl acetate | 1.2 |
| Ethyl butyrate | 1.2 |
| Butyl butyrate | 1.2 |
| Propyl propionate | 1.2 |
| Diethyl carbonate | 1.2 |
| Cyclopentanone | 1.2 |
| Cyclohexanone | 1.2 |
| 1-Nitropropane | 1.2 |
| 2-Nitropropane | 1.2 |

I have discovered that certain organic compounds will greatly improve the relative volatility of 2-butanol to t-amyl alcohol and permit the separation of 2-butanol from t-amyl alcohol by rectification when employed as the agent in extractive distillation. Table 2 lists the compounds that I have found to be effective. They are acetophenone, adiponitrile, methyl caproate, ethyl caproate, propyl caproate, hexyl acetate, ethyl butyrate, butyl butyrate, propyl propionate, diethyl carbonate, cyclopentanone, cyclohexanone, 1-nitropropane and 2-nitropropane.

THE USEFULNESS OF THE INVENTION

The usefulness or utility of this invention can be demonstrated by referring to the data presented in Tables 1 and 2. All of the successful agents show that 2-butanol can be separated from t-amyl alcohol by means of extractive distillation in a rectification column and that the ease of separation as measured by relative volatility is considerable.

WORKING EXAMPLES

Example 1

Eighty grams of 2-butanol, 20 grams of t-amyl alcohol and 50 grams of methyl caproate were charged to a vapor-liquid equilbrium still and refluxed for thirteen hours. Analysis indicated a vapor composition of 81.2% 2-butanol, 18.8% t-amyl alcohol; a liquid composition of 77.4% 2-butanol, 22.6% t-amyl alcohol. This is a relative volatility of 1.25.

Example 2

Twenty grams of 2-butanol, 80 grams of t-amyl alcohol and 50 grams of adiponitrile were charged to a vapor-liquid equilibrium still and refluxed for twelve hours. Analysis indicated a vapor composition of 18.6% 2-butanol, 81.4% t-amyl alcohol; a liquid composition of 14.8% 2-butanol, 85.2% t-amyl alcohol. This is a relative volatility of 1.32.

I claim:

1. A method for recovering 2-butanol from a mixture of 2-butanol and t-amyl alcohol which comprises distilling a mixture of 2-butanol and t-amyl alcohol in the presence of about one part by weight of an extractive agent per part of 2-butanol—t-amyl alcohol mixture, recovering 2-butanol as overhead product and obtaining the t-amyl alcohol and the extractive agent as bottoms product, wherein said extractive agent consists of one material selected from the group consisting of acetophenone, adiponitrile, methyl caproate, ethyl caproate, propyl caproate, hexyl acetate, ethyl butyrate, butyl butyrate, propyl propionate, diethyl carbonate, cyclopentanone, cyclohexanone, 1-nitropropane and 2-nitropropane.

* * * * *